(12) United States Patent
Poechlauer et al.

(10) Patent No.: US 9,249,088 B2
(45) Date of Patent: Feb. 2, 2016

(54) CONTINUOUS PRODUCTION AND REACTION OF A DIAZO COMPOUND

(75) Inventors: Peter Poechlauer, Echt (NL); Rafael Wilhelmus Elisabeth Ghislain Reintjens, Echt (NL); Hubertus Johannes Adrianus Dielemans, Echt (NL); Mehul Thathagar, Echt (NL); Jeroen Hubertina Gerardus Konings, Echt (NL)

(73) Assignee: DPx Holdings B.V., Amsterdam (NL)

( * ) Notice: Subject to any disclaimer, the term of this patent is extended or adjusted under 35 U.S.C. 154(b) by 39 days.

(21) Appl. No.: 13/879,889

(22) PCT Filed: Nov. 1, 2011

(86) PCT No.: PCT/EP2011/069186
§ 371 (c)(1),
(2), (4) Date: Dec. 27, 2013

(87) PCT Pub. No.: WO2012/059485
PCT Pub. Date: May 10, 2012

(65) Prior Publication Data
US 2014/0100360 A1    Apr. 10, 2014

(30) Foreign Application Priority Data
Nov. 1, 2010 (EP) .................................... 10189601

(51) Int. Cl.
| C07C 245/16 | (2006.01) |
| C07C 67/00 | (2006.01) |
| C07C 245/14 | (2006.01) |
| C07D 231/06 | (2006.01) |

(52) U.S. Cl.
CPC ............... *C07C 245/16* (2013.01); *C07C 67/00* (2013.01); *C07C 245/14* (2013.01); *C07D 231/06* (2013.01)

(58) Field of Classification Search
CPC .................................................. C07C 245/16
USPC ........................................................ 534/565
See application file for complete search history.

(56) References Cited

U.S. PATENT DOCUMENTS

| 5,854,405 | A | 12/1998 | Archibald et al. |
| 6,962,983 | B2 | 11/2005 | Warr et al. |
| 7,591,747 | B2 | 9/2009 | Raghavan et al. |
| 2002/0188112 | A1 | 12/2002 | Warr et al. |
| 2007/0249817 | A1 | 10/2007 | Haase |

FOREIGN PATENT DOCUMENTS

| CN | 1980885 A | 6/2007 |
| DE | 10 2004 030371 | 1/2006 |
| GB | 2 357 501 | 6/2001 |
| JP | 2007-519510 A | 7/2007 |
| WO | 2005/063379 A1 | 7/2005 |

OTHER PUBLICATIONS

International Search Report for PCT/EP2011/069186 mailed May 18, 2012.
Written Opinion of the International Searching Authority mailed May 18, 2012.
M. Struemphel et al., "Making Diszomethane Accessible for R&D and Industry: Generation and Direct Conversion in a Continuous Micro-reactor set-up", Jan. 1, 2008, Green Chemistry, 3 Pages.
M. Struemphel et al., "Continuous Production of the Diazomethane Precursor N-Methyl-N-nitroso-p-toluenesulfonamide: Batch Optimization Setup", Organic Process Research & Development, vol. 13, No. 5, Sep. 18, 2009, pp. 1014-1021.
Black, T. H. et al. Aldrichimica Acta The Preparation and Reactions of Diazomethane., Triflic Acid and it Derivatives, 1983, 16 (1), 1-79.
Fogler, H. Scott: 'Elements of Chemical Reaction Engineering', 2005, Prentice-Hall, 4th ed.
Michael Struempel et al: 11 Continuous Production of the Diazomethane Precursor N-Methyl- N- nitroso-ptoluenesulfonamide: Batch Optimization and Transfer into a Microreactor Setup, Organic Process Research & Development, ol. 13, No. 5, Sep. 18, 2009, pp. 1014-1021, XP055003346, whole document; relevant claims 1-14 [A].
Struempel M et al: 11 Making diazomethane accessible for R&D and industry:generation and direct conversion in a continuous microreactor set-up, Jan. 1, 2008, Green Chemistry, Royal Society of Chemistry, Cambridge, GB, pp. 41-43, XP009149804, whole document; relevant claims 1-14 [A].
Lobbecke, et al., "The Potential of Microeactors for the Synthesis of Energetic Materials,:"Chemie Ingenieur Technik, 2004, 76 (9), 1326, 5.
V. Hessel and H. Lowe, "Mikroverfahrenstechnik: Komponenten, Anlagen-konzeption, Anwenderakzeptanz", Chem. Ing. Techn. 74, 2002, pp. 17-30.

(Continued)

*Primary Examiner* — Robert Havlin
(74) *Attorney, Agent, or Firm* — Pierce Atwood LLP; Raymond G. Arner (57) ABSTRACT

A process for producing a reaction product of a diazo compound, which process comprises: a. continuously supplying to a first reactor a precursor of a diazo compound; a water-miscible solvent; a base and water; b. mixing the precursor of a diazo compound; the water-miscible solvent; the base and water to generate a diazo compound; c. continuously removing from the first reactor, through a hydrophobic membrane, into a second reactor the formed diazo compound; d. continuously removing from the first reactor all reaction products that have not passed into the second reactor; e. continuously supplying to the second reactor a substrate in a non-water-miscible solvent; f. mixing the above components to generate a reaction product of a diazo compound; and g. continuously removing from the second reactor the non-water-miscible solvent and the reaction product of the diazo compound, and apparatus suitable for carrying out such a process.

14 Claims, 2 Drawing Sheets

(56) References Cited

OTHER PUBLICATIONS

V. Hessel and H. Lowe, "Mikroverfahrenstechnik: Komponenten, Anlagen-konzeption, Anwenderakzeptanz", Chem. Ing. Techn. 74, 2002, pp. 185-207.
V. Hessel and H. Lowe, "Mikroverfahrenstechnik: Komponenten, Anlagen-konzeption, Anwenderakzeptanz", Chem. Ing. Techn. 74, 2002, pp. 381-400.
Isono, et al., "Application of Hydrophobic Membrane for Alcohol Separation from Alcohol/Aqueous Biphase Mixture," Separation Purfication Technology, 17(1), 1999, 77-82.
J.A. Apffel, Li.A.Th Brinkman and R.W. Frei, Chromatographia 18(1), 1984, 5-10.
27886-EP-EPA Sep. 19, 2011 Search Report, 59 pages.
Decision to Grant a European Patent for EP-11778584.0, mailed Nov. 20, 2014, 2 pages.
Notification of Registration and Granting a Patent Right for CN-201180052651.X, mailed Aug. 11, 2015, 5 pages.
Office Action for CN-201180052651.X, mailed Feb. 15, 2015, 7 pages.
Office Action for CN-201180052651.X, mailed Sep. 19, 2014, 9 pages.
Office Action for CN-201180052651.X, mailed Mar. 27, 2014, 12 pages.
Notice of Reasons for Rejection for JP-2013-535464, mailed May 26, 2015, 6 pages.
Hessel, V., et al., "Mikroverfahrenstechnik", Chemie Ingenieur Technik, Volume: 76, Issue No. 9, pp. 1326-1327, 2004.
International Preliminary Report on Patentability for PCT/EP2011/069186, mailed May 16, 2013, 5 pages.

CONTINUOUS PRODUCTION AND REACTION OF A DIAZO COMPOUND

This application is the U.S. national phase of International Application No. PCT/EP2011/069186 filed 1 Nov. 2011 which designated the U.S. and claims priority to EP 10189601.7 filed 1 Nov. 2010, the entire contents of each of which are hereby incorporated by reference.

The present invention concerns the continuous reaction and production of diazo compounds, and apparatus for the above uses.

Diazo compounds such as diazomethane are very versatile reagents for the preparation of both carbon-carbon and carbon-heteroatom bonds. Diazomethane is one of the most common reagents to introduce methyl groups, for example in the preparation of methyl esters from the corresponding carboxylic acids. It is further used in the alkylation of phenols, enols, and heteroatoms such as nitrogen and sulfur. Diazomethane has also been used in cycloalkanone ring expansion; preparation of α-diazo ketones; pyrazoline formation; and Pd-catalyzed cyclopropanation.

Despite its synthetic versatility, Diazomethane is hardly seen in industrial production due to the huge safety risks involved. These risks comprise its toxicity, its carcinogenic properties and its explosive potential.

Diazomethane and diazoethane can be produced from the N-nitroso-N-alkyl-urea derivatives. Additionally syntheses of diazomethane from N-methyl-N'-nitro-N-nitrosoguanidine (MNNG) and N-methyl-N-nitroso-p-toluenesulfonamide (Diazald®) are known.

N-Nitroso-N-methylurea (NMU) is a carcinogen, mutagen, and teratogen. NMU is an alkylating agent, and exhibits its toxicity by transferring its methyl group to nucleobases in nucleic acids. NMU is the traditional precursor in the synthesis of diazomethane. However, since it is unstable at temperatures beyond 20° C. and shock-sensitive to a degree, for this purpose it has become obsolete and replaced by other (N-methyl)nitrosamides.

MNNG is toxic, a severe irritant, a carcinogen, and a potent mutagen. While Diazald® is also considered to be a severe irritant, it has not demonstrated the acute toxicity of MNNG.

As both diazo compounds and their precursors are hazardous, unstable compounds, a number of methods have been suggested to circumvent problems related to their handling.

U.S. Pat. No. 6,962,983 B2 discloses a method for the production of diazomethane comprising the steps of a) feeding a base and a diazomethane precursor into a reactor vessel; b) generating gaseous diazomethane by allowing the base and the diazomethane precursor to react; and c) removing the diazomethane using a diluent gas. DE 102004030371 discloses a process for the production of gaseous diazoalkanes in which a diazoalkane precursor in a first solvent and a base in a second solvent are mixed in a reactor to form the diazoalkane which is removed under reduced pressure as a gas. In Chemie Ingenieur Technik, 2004, 76 (9), 1326, Loebbecke et. al. describe a microreactor for the mixing of a diazomethane precursor and a base. The formed reaction mixture containing diazomethane is quenched directly into a solution containing a reaction partner for diazomethane. These processes reduce the risk of handling large quantities or high concentrations of diazomethane, but it still bear the risk of handling hazardous diazomethane precursors.

U.S. Pat. No. 5,854,405 discloses a process for producing diazomethane by dissolving an N-methyl-N-nitroso amine in a mixture of a water-miscible organic solvent that dissolves the N-methyl-N-nitroso amine and a water-immiscible organic solvent that dissolves diazomethane and combining a stream of this solution with a stream of an aqueous inorganic base, allowing the aqueous and organic phases to settle after a suitable residence time and separating the phases, all on a continuous basis. Further, when N-methyl-N-nitroso urea is used as the amine, the diazomethane process is preceded by a continuous nitrosation involving combining aqueous solutions of methyl urea and a nitrite salt with an organic solution of a mineral or organic acid, the solvent in the organic solution being a mixture of the two organic solvents referred to above, allowing the aqueous and the organic phases to settle after a suitable residence time, and separating the phases, all on a continuous basis. The resulting organic phase is continuously fed to the diazomethane stages. This procedure describes a continuous production of both the precursor of diazomethane and diazomethane itself. However, it still bears the risks of performing various unit operations (settling and separating phases) on solutions of the precursor and the diazomethane.

Streumpel et al. in Organic Process Research & Development 2009, 13, 1014-1021 describe a process for the production of Diazald® in a microreactor system. The process involves two continuous reaction steps (amidation of p-toluene sulfonyl chloride and nitrosation of the resulting N-methyl-N-nitroso-p-toluene-sulfonamide, each of which terminate in a batch container to collect larger quantities before carrying out subsequent step of phase separation in a separating funnel. Thus there is still a risk in carrying out these separations on solutions of a precursor and of diazomethane.

In Green Chem., 2008, 10, 41-43, Streumpel et al. describe formation of diazomethane from Diazald® and subsequent reaction of diazomethane with benzoic acid, through the use of microreactor technology. The resulting product stream contains the desired product of benzoic acid methyl ester, together with a mixture of solvents and waste products. The method therefore does not avoid the handling of a precursor of diazomethane. It also has the drawback of yielding a product stream requiring substantial work up to remove waste products.

There is accordingly a need for a process of efficiently producing in good yield reaction products of diazo compounds directly from the respective precursors, by continuous formation of the diazo compound followed by continuous reaction of the diazo compound to form a reaction product devoid of the hazardous properties of the diazo compound. In such a process the quantities of the hazardous precursor and the hazardous diazo compound should be minimized.

It has now been found that the above object can be reached by a process in which the continuous generation of the diazo compound and the continuous reaction of the diazo compound with a substrate are carried out in a continuously operated membrane reactor, in which the membrane selectively allows diazomethane to pass.

Accordingly, the present invention provides a process for producing a reaction product of a diazo compound, which process comprises:
  a) continuously supplying to a first reactor a precursor of a diazo compound; a water-miscible solvent; a base and water;
  b) mixing the precursor of a diazo compound; the water-miscible solvent; the base and water to generate a diazo compound;
  c) continuously removing from the first reactor, through a hydrophobic membrane, into a second reactor the formed diazo compound;
  d) continuously removing from the first reactor all reaction products that have not passed into the second reactor;
  e) continuously supplying to the second reactor a substrate in a non-water-miscible solvent;

f) mixing the above components to generate a reaction product of a diazo compound; and g) continuously removing from the second reactor the non-water-miscible solvent and the reaction product of the diazo compound.

Above components in step f) are components entered into the second reactor. That is the formed diazo compound and the substrate in the non-water-miscible solvent.

Further, the present invention provides apparatus suitable for carrying out the above process, said apparatus comprising a first reactor separated from a second reactor by a hydrophobic membrane.

Continuously operated reactors comprising a membrane are known, for example, in Fogler, H. Scott, Elements of Chemical Reaction Engineering, 4rd Ed. Prentice-Hall: Upper Saddle River, N.J., 2005.

An advantage of carrying out the continuous formation of a diazo compound, followed by the continuous reaction of the diazo compound to form a product of a diazo compound is the improved safety of the process, since no significant volume of the diazo compound is present at any one time. Further, such a process does not require high dilution of diazo compound, and is therefore relatively small scale, and therefore lower cost.

As used herein diazo compound means any compound comprising the terminal group $C=N^-=N^+$. Accordingly, reaction product of a diazo compound means the product of the reaction between a diazo compound and a substrate. Typically, the diazo compound is diazomethane or diazoethane.

Suitable substrates are those that will react with the diazo compound to form the desired product at a sufficient rate to allow the concentration of the diazo compound in the second reactor to remain low and to inhibit the escape of high (therefore hazardous) concentrations of the diazo compound leaving the second reactor. Examples of such substrates are described in, for example, Black, T. H. et al. Aldrichimica Acta, 1983, 16 (1), 3. Suitable substrates include olefins, for example styrene and ethyl acrylate; ketones, for example cyclohexanone; aldehydes, for example benzaldehyde; carboxylic acids, for example acetic acid and benzoic acid; and carboxylic acid chlorides, for example butyryl chloride or phenylacetyl chloride. Typically, the substrate is an olefin, a ketone, an aldehyde, a carboxylic acid or a carboxylic acid chloride.

A precursor of a diazo compound is a compound that may be reacted to form a diazo compound. Typically the precursor of the diazo compound is an N-alkyl-N-nitroso-toluene-sulfonamide, N-alkyl-N-nitroso-urea, or a N-alkyl-N'-nitro-N-nitrosoguanidine. Preferably, it is N-methyl-N-nitroso-urea, N-ethyl-N-nitroso-urea, N-methyl-N-nitroso-toluene-sulfonamide, N-ethyl-N-nitroso-toluenesulfonamide, N-methyl-N'-nitro-N-nitroso-guanidine, N-ethyl-N'-nitro-N-nitroso-guanidine. Precursors of diazo compounds are known and commercially available or can be produced batch wise by known procedures.

The precursor of a diazo compound may be dissolved in the water-miscible solvent, forming a first feed stream. The base may be dissolved in either water or a water-miscible solvent, or both, forming a second feed stream.

A suitable water-miscible solvent dissolves sufficient quantities of the precursor and the base to allow quick reaction of the precursor with the base to form the diazo compound. A suitable water miscible solvent will not react with the diazo compound or the substrate. Typical water miscible solvents are able to diffuse through the hydrophobic membrane. Examples of suitable solvents are alcohols, for example methanol, ethanol, butanol or carbitol; and polyols, for example ethylene glycol, propylene glycol or glycerol or mixtures thereof. Typically, the water miscible solvent is butanol, ethanol, tetrahydrofuran, DMSO or a mixture thereof.

A suitable base is an aqueous base, for example an aqueous alkali hydroxide solution. Typically the base is sodium hydroxide, potassium hydroxide or a mixture thereof. A typical concentration of a base is from 2 to 50 weight %.

As used herein a reactor is typically a micro- or minireactor. Each of these differs only from conventional size reactors in the dimensions and constructions of the reaction channel structures. A micro- or minireactor is a miniaturized reactor with characteristic dimensions (channel width and depth, or plate width) in micrometers (microreactor) to millimeters (minireactor). The characteristic dimensions are the dimensions perpendicular to the flow of the reaction mixture through the microreactor. The characteristic dimensions are for example from 0.1 mm to 20 mm; typically from 1 to 10 mm, for example 2 to 5 mm.

Preferably, a micro- or minireactor is defined as a reactor having a channel with a hydraulic diameter of 20 mm or less. The hydraulic diameter $D_h$ is defined as 4A/U, wherein A is the cross sectional area of the reactor channel and U is the perimeter of said cross section.

Such reactors are described in the art, for example, in: V. Hessel and H. Löwe, "Mikroverfahrenstechnik: Komponenten, Anlagen-konzeption, Anwenderakzeptanz", Chem. Ing. Techn. 74, 2002, pages 17-30, 185-207 and 381-400. S. Löbbecke et al., "The Potential of Microreactors for the Synthesis of Energetic Materials", 31$^{st}$ Int. Annu. Conf. ICT; Energetic Materials-Analysis, Diagnostics and Testing, 33, 27-30 Jun. 2000, Karlsruhe, Germany. Microreactors, micromixers, micro-heat-exchangers have been developed, for example in Germany (i.e.: IMM, Mainz, and Forschungszentrum Karlsruhe) and in the USA (i.e.: MIT and DuPont).

An advantage of using a micro- or minireactor is that they have very effective heat transfer to and from the reactor, allowing good control of a highly exothermic reaction. Also the volumes of reagents and products are low, meaning that safety is improved because any explosion is only on a small scale.

Mixing of streams of reagents is typically carried out by T-mixers, which are known in the art. Typically in step a) of the process described above the precursor of a diazo compound; the water-miscible solvent; the base and water are first mixed to form a single feed stream, and then said feed stream is supplied to the first reactor.

The first and second reactors are separated by a hydrophobic membrane. The hydrophobic membrane itself may form the division between the first and second reactors. In that case this may comprise a single vessel, divided in two by a hydrophobic membrane.

A suitable membrane will allow diffusion of the formed diazo compound from the first reactor into the second reactor while inhibiting other components of the reaction mixture from passing from the first reactor to the second reactor. The membrane is therefore in effect selective for the diazo compound.

The membrane must withstand the conditions of the reaction mixtures in each of the first and second reactors, without affecting either the reactions, or being affected itself. Suitable membranes will not initiate or accelerate the decay of the diazo compound. Examples of suitable membranes are polymer membranes such as polypropylene-based, PTFE-based or polyethylene-based membranes. Membranes capable of separating aqueous and organic phases have been described. See, for example J. A. Apffel, U. A. Th Brinkman and R. W. Frei, Chromatographia 18(1), 1984, 5-10; and Separation and Purification Technology, 17(1), 1999, 77-82. Typically the membrane is a microporous membrane comprising polypropylene, polytetrafluoroethylene (PTFE) or polyethylene.

The membrane surface area should be sufficiently large for the volume of the first reactor to allow quick removal of the diazo compound through the membrane. In addition there may be one or more membranes present. Each membrane may have a different form; it may be, for example, flat or tubular in shape.

Mixing may be by any suitable means known in the art. This may be active, for example by mechanical agitation, or passive, for example simply by turbulence of the feed stream entering the reactor.

The process as described above, typically further comprises, h) continuously supplying to a third reactor, an N-alkyl compound, an acid and an aqueous nitrite solution;
i) mixing the N-alkyl compound, acid and aqueous nitrite solution to generate a precursor of a diazo compound; and
j) continuously removing from the third reactor the precursor of a diazo compound and continuously supplying it to step (a).

A particular advantage of combining the generation of the precursor of a diazo compound with direct conversion to a diazo compound and then further reaction to a reaction product of a diazo compound is the further improved safety of the process, since no significant volume of the hazardous precursor of the diazo compound is present at any one time. In other words, only harmless starting materials and harmless final products are present in substantial amounts whereas the hazardous precursor of the diazo compound as well as the diazo compound itself is only present in small amounts inside the reactors. A particularly large improvement in manufacturing safety for personnel and environment is therefore realized in this embodiment of the invention.

Preferably, the process comprises in step (h) continuously supplying a non-water-miscible solvent to the third reactor; and, in step (j), optionally separating the aqueous phase from the precursor of the diazo compound and non-water-miscible solvent before supplying the precursor of the diazo compound to step (a). Use of a non-water-miscible solvent facilitates separation of the precursor of the diazo compound from aqueous byproducts at this stage.

The N-alkyl compound is typically dissolved in water. The N-alkyl compound and aqueous nitrite may be mixed prior to entry to the third reactor, to form a single feed stream. The acid is typically dissolved in an organic solvent.

Typically the apparatus comprises a third reactor connected upstream from the first reactor. Preferably, the apparatus further comprises a separator comprising a hydrophobic membrane between the third reactor and the first reactor. More preferably, each of the first, second and, where present, third reactor is a minireactor or a microreactor.

In one embodiment of the present invention, a solution of an N-alkyl-N-nitroso toluene-sulfonamide suspended in ethanol or ethylene glycol and aqueous sodium hydroxide is continuously added and mixed in a first reactor which is separated by a PTFE membrane from a second reactor. A stream comprising an olefin and a hydrocarbon solvent are continuously added to the second reactor. The effluents from the first reactor are discarded; the effluents from the second reactor contain the reaction product of a diazo alkane and are processed to isolate the product of a diazo alkane.

In another embodiment of the present invention, a continuous stream of an N-alkyl-N-nitroso toluene-sulfonamide and a continuous stream of a suitable base as described above are reacted in a first reactor to form a diazo compound. To this stream are then added continuous streams of a suitable organic solvent and water or an aqueous salt solution to effect quick continuous phase separation and dissolution of the diazo compound in the organic phase. The organic phase then passes the membrane to enter the second reactor and reacts with a solution of the substrate in an organic solvent. Again, the effluents from the first reactor are discarded; the effluents from the second reactor contain the product of a diazo alkane and are processed to isolate the product of a diazo alkane.

A further embodiment of the process comprises a combination of one of the abovementioned continuous membrane processes to generate a reaction product of a diazo compound with the continuous generation of the N-alkyl-N-nitroso compound (a precursor of the diazo compound) from the corresponding N-alkyl compound.

In this embodiment a continuous stream of the respective N-alkyl-N-nitroso compound in a suitable solvent is created by continuous mixing of a stream containing the N-alkyl compound and a suitable acid with a stream containing aqueous nitrite solution in a reactor. Flow ratios are selected to achieve a high degree of conversion of the N-alkyl compound to the N-alkyl-N-nitroso compound. The solvent is selected to allow the N-alkyl-N-nitroso compound to dissolve in the solvent while the acid and by products (such as unreacted N-alkyl compound and nitrite) remain in the aqueous phase. Separation of the aqueous and organic phases may be effected by specific gravity difference or preferably by a membrane allowing the organic solvent containing the N-alkyl-N-nitroso compound to pass while retaining the aqueous phase. Furthermore the solvent is selected to allow immediate usage of the solution of the N-alkyl-N-nitroso compound in the process generating the product of the diazoalkane.

Figure 1:
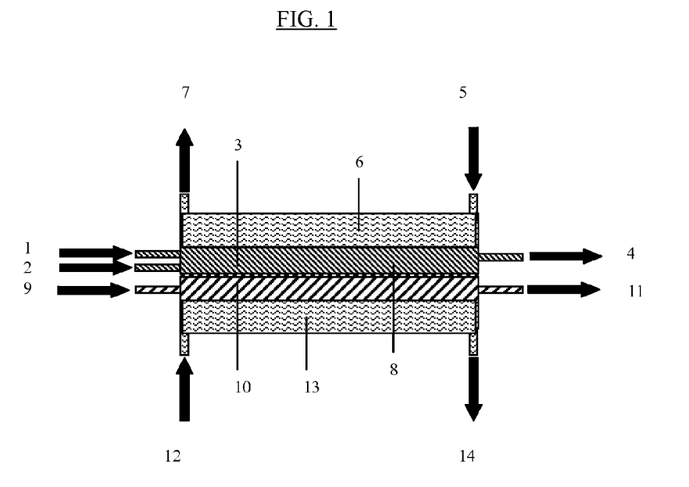
FIG. 1 depicts apparatus of the present invention suitable for generating a diazo compound from a precursor and reacting the diazo compound to produce a reaction product of a diazo compound.

FIG. 1 depicts an apparatus of the present invention. In particular it is suitable for performing a process according to Example 1. (1) and (2) are inlets to a first reactor, (3). A first feed stream comprising a precursor of a diazo compound; and a water-miscible solvent passes through inlet (1). A second feed stream comprising a base and water enters via inlet (2). Formed diazo compound and part of the water-miscible solvent pass through hydrophobic membrane (8) into a second reactor (10). Waste products pass through the outlet (4). Heating/cooling jacket (6) has an inlet (5) and outlet (7), through which a thermostatic fluid passes. A substrate in a non-water miscible solvent is passed into the second reactor through inlet (9) and the product of a diazo compound exits through outlet (11). Heating/cooling jacket (13) has an inlet (12) and outlet (14), through which a thermostatic fluid passes. The heating/cooling jackets (6) and (13) may together comprise one heating/cooling jacket.

Figure 2:
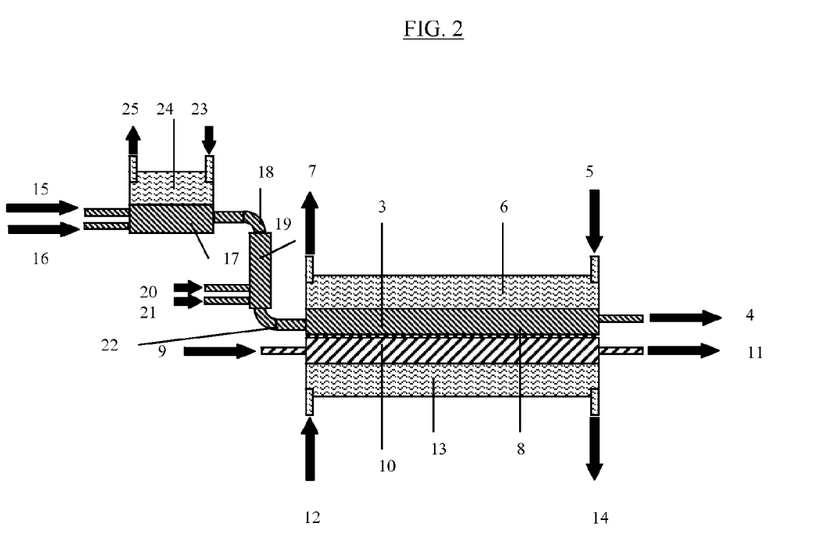
FIG. 2 depicts apparatus of the present invention, which in addition to that of FIG. 1, is suitable for forming a precursor of the diazo compound.

FIG. 2 depicts a further apparatus according to the present invention. In particular it is suitable for performing a process according to Example 2. Components 3 to 14 operate as described with respect to FIG. 1. In addition, a stream comprising an N-alkyl compound and a stream comprising an aqueous nitrite solution enters inlet (15) and an acid enters inlet (16). These are mixed in mixing zone (17). The product precursor of a diazo compound exits through connection (18) into mixer (19). A non-water-miscible solvent enters inlet (20) and a base enters inlet (21) also into mixer (19). The fluid passes through connection (22) and becomes the feed for reactor (3). A thermostatic fluid is passed through inlet (23) into cooling chamber (24) and exits through outlet (25).

Figure 3:
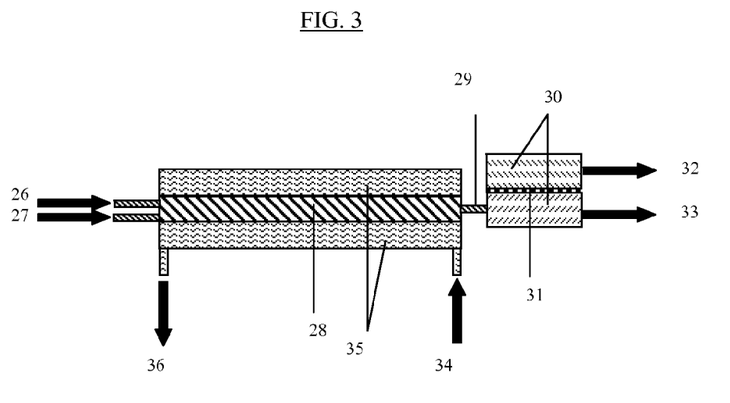
FIG. 3 depicts an apparatus for providing constant flow of a precursor of a diazo compound.

FIG. 3 depicts an apparatus for providing constant flow of a precursor of a diazo compound. A stream comprising an N-alkyl compound and an aqueous nitrite solution passes through inlet (26) and a stream comprising an acid passes through inlet (27) into the reactor (28). The product precursor of a diazo compound passes through connector (29) into separator (30). The aqueous phase exits through outlet (33); whereas the organic phase comprising the precursor of the diazo compound passes through membrane (31) and exits through outlet (32). A thermostatic fluid is passed through inlet (34) into heating/cooling jacket (35) and exits through outlet (36). The precursor for the diazo compound may be isolated from stream of outlet (32) or the stream from outlet 32 may be used for feed stream into inlet (1) to first reactor in FIG. 1.

The present invention is illustrated by but not limited to the following examples.

EXAMPLE 1

An apparatus was set up according to FIG. 1, comprising temperature-controlled first reactor and second reactor and a hydrophobic (polypropylene) membrane separating said reactors. The apparatus was continuously operated at the flow rates listed in Table 1. The thermostatic fluid entries are charged with a stream of 100 g/min of water at Temperature T2 listed in Table 1.

One of the 2 entries of the first reactor was charged with the indicated flow rate of Diazald® in the indicated solvent. The other entry of the first reactor was charged with the indicated flow rate of aqueous potassium hydroxide (KOH) solution.

The entry of the second reactor was charged with the indicated flow rate of benzoic acid (BzCOOH) in the indicated solvent. (MTBE is methyl tert-butyl ether.)

The dimensions of the membrane unit were chosen to provide sufficient membrane area separating the first reactor and the second reactor to allow the formed diazomethane to diffuse from the first reactor to the second reactor, and to effect a residence time of 1 minute of the reaction mixture in the first reactor and 3 minutes of the reaction mixture in the second reactor. The reactor comprised a tube having internal diameter of 3.2 mm and length of 1 m. Inside the tube was positioned a tube of hydrophobic membrane having an internal diameter of 1.5 mm and length of 1 m. The first reactor is the volume between the outer tube and the inner tube and the second reactor is the volume inside the inner tube of the hydrophobic membrane. The area of the hydrophobic membrane is 47 cm$^2$.

Upon continuous operation, the stream at the exit of the first reactor was continuously mixed with a tenfold volumetric excess of 10 w/w % aqueous acetic acid solution to effect complete destruction of any trace of diazo compound that may have left the first reactor.

TABLE 1

| 0.4M Diazald ®/ solvent 1 ml/min solvent | 1.2M KOH/ solvent 0.5 ml/min solvent | Eq. BzCOOH | 0.6M BzCOOH/ solvent (w/w) | T2 ° C. | Yield methyl benzoate % |
|---|---|---|---|---|---|
| carbitol | Water | 5.0 | MTBE-heptane (50/50) | 20 | 0 |
| carbitol | Water/carbitol | 5.0 | MTBE-heptane (50/50) | 40 | 11 |

The results show that diazomethane can be generated and reacted with benzoic acid to form methyl benzoate, while the benzoic acid in the second reactor is not neutralized by the potassium hydroxide solution in the first reactor.

EXAMPLE 2

To improve the extraction efficiency, further experiments were made in a slightly modified plant.

Apparatus was set up according to FIG. 2, comprising:

a mixing zone for a precursor of the diazo compound and a base;

mixing zones to add an organic solvent and water or an aqueous solution to this stream, which then enters the temperature-controlled first reactor;

a second reactor; and a hydrophobic membrane separating said reactors.

The apparatus was continuously operated at the flow rates listed in Table 2.

TABLE 2

| 0.4M Diazald®/ solvent 1 ml/min solvent | 1.2M KOH/ solvent 0.5 ml/min solvent | Eq. BzCO—OH | 0.6M BzCO—OH/ solvent (w/w) | NaCl/water at entry aqueous solution ml/min | MTBE/heptane at entry aqueous solution ml/min | T1 °C. | T2 °C. | Yield methyl benzoate % |
|---|---|---|---|---|---|---|---|---|
| carbitol | 2-propanol | 4.0 | MTBE-heptane (50/50) | 2 | 1 | 60 | 20 | 35 |
| carbitol | 2-propanol | 4.0 | MTBE-heptane (50/50) | 2 | 2 | 60 | 20 | 47 |
| carbitol | 2-propanol | 2.67 | MTBE-heptane (50/50) | 2 | 3 | 60 | 20 | 60 |
| carbitol | 2-propanol | 1.33 | MTBE-heptane (50/50) | 2 | 4 | 60 | 20 | 62 |
| carbitol | 2-propanol | 1.25 | MTBE-heptane (50/50) | 2 | 3 | 60 | 2 | 61 |

The example shows that addition of aqueous solution and organic solvent after mixing of Diazald® and KOH improves the extraction of the diazomethane into the organic solvent and its passage through the membrane to react with benzoic acid. A small excess of benzoic acid is required to reach a yield comparable to literature (A. Stark et. al., Green Chem., 2008, 10, pages 41-43) values achieved with much higher excess of benzoic acid without a membrane.

EXAMPLE 3

The apparatus as described in Example 1 is combined with apparatus as depicted in FIG. 3, providing a continuous stream of a 10 w/w solution of N-methyl-N-nitroso-toluene-sulfonamide in tetrahydrofuran (organic solvent). This stream is continuously prepared as follows:

A continuous stream of 10 g/min of tetrahydrofuran containing 10 w/w % of N-methyl-toluenesulfonamide and 5 w/w % of sodium nitrite is mixed with a continuous stream of 5 g/min of 3M HCl in a third reactor during a residence time of 2 minutes. The effluent of the third reactor is separated continuously, either by gravity or by means of a membrane, into the organic and the aqueous phase. The aqueous phase was discarded and the organic phase continuously charged to one entry of the first reactor as described in Example 1.

Continuous operation of the combined processes delivers a stream which is free of the diazo compound and is ready for further downstream processing.

EXAMPLE 4

In a continuous reactor setup as described in Example 2, the cycloaddition of diazomethane to methyl acrylate was performed.

Diazomethane is prepared by mixing 1.2M KOH/2-propanol (0.5 ml/min) and 0.4M Diazald®/carbitol solution (1.0 ml/min) and reacting them at 60° C. The reaction time was 85 sec. To the homogeneous solution were added continuous streams of NaCl-water (2.0 ml/min) and MTBE/heptane (50/50) (3.0 ml/min) to extract the diazomethane to the organic layer. The organic layer including the diazomethane passed through the membrane where it reacted with the 0.4M methyl acrylate/MTBE-heptane solution at reaction temperature T2 (residence time 49-74 sec). The organic solution was analysed via GC-MS where the product molecular mass was confirmed (mass 128). Results are shown in Table 3.

TABLE 3

| 0.4M Diazald®/ solvent 1.0 ml/min | 1.2M KOH/ solvent 0.5 ml/min | methylacrylate Eq | 0.4M methylacrylate/ solvent | Reacton temp. T2 °C. | Yield % |
|---|---|---|---|---|---|
| Carbitol | 2-propanol | 2 | MTBE/heptane (50/50) | 20 | 39 |
| Carbitol | 2-propanol | 1 | MTBE/heptane (50/50) | 40 | 40 |

Results: although methyl acrylate reacted slower than benzoic acid, a considerable yield was generated by reaction with diazomethane solution transgressing the membrane. No hydrolysis product of methyl acrylate was detected.

EXAMPLE 5

In a continuous reactor setup as described in Example 2 the cycloaddition of diazomethane to styrene was performed.

Diazomethane was prepared by mixing 1.2M KOH/2-propanol (0.5 ml/min) and 0.4M Diazald®/carbitol solution (1.0 ml/min) and reacting them at 60° C. The reaction time was 85 sec. To the homogeneous solution were added continuous streams of NaCl-water (2.0 ml/min) and MTBE/heptane (50/50) (3.0 ml/min) to extract the diazomethane to the organic layer. The organic layer including the diazomethane passed through the membrane where it reacted with the 0.5M styrene/MTBE-heptane solution at reaction temperature T2 (residence time 49-74 sec). The organic solution is analysed via ¹H-NMR. Results are shown in Table 4.

TABLE 4

| 0.4M Diazald®/ solvent 1.0 ml/min | 1.2M KOH/ solvent 0.5 ml/min | styrene Eq | 0.5M styrene/ solvent | Reacton temp. T2 °C. | Residence time sec. | Yield (diazo- methane) % |
|---|---|---|---|---|---|---|
| carbitol | 2-propanol | 1.25 | MTBE/heptane (50/50) | 2 | 74 | 47 |
| carbitol | 2-propanol | 2.50 | MTBE/heptane (50/50) | 28 | 59 | 70 |
| carbitol | 2-propanol | 1.25 | MTBE/heptane (50/50) | 50 | 74 | 13 |

During the synthesis a solid was formed at higher temperature inside the membrane reactor, which indicates polymerization. The higher the reaction temperature the more solid was formed. Therefore the yield decreases at higher temperature. No isomerisation of the double bond in the product was detected. The reaction is still slower than the reaction with methyl acrylate. Complete consumption of the diazomethane by reaction with styrene takes several hours at 24° C. The cycloaddition product was detected in ~70% yield.

EXAMPLE 6

In a continuous reactor setup as described in Example 2 the cycloaddition of diazomethane to beta-nitro-styrene was performed. Diazomethane was prepared by mixing 1.2M KOH/2-propanol (0.5 ml/min) and 0.4M Diazald®/carbitol solution (1.0 ml/min) and reacting them at 60° C. The reaction time was 85 sec. To the homogeneous solution were added continuous streams of NaCl-water (2.0 ml/min) and MTBE/heptane (50/50) (3.0 ml/min) to extract the diazomethane to the organic layer. The organic layer including the diazomethane passed through the membrane where it reacted with the 0.5M beta-nitro-styrene/MTBE-heptane solution at a reaction temperature T2 (residence time 49-74 sec). The organic solution was analysed via ¹H-NMR. Results are shown in Table 5.

TABLE 5

| 0.4M Diazald®/ solvent 1.0 ml/min | 1.2M KOH/ solvent 0.5 ml/min | Beta- nitro- styrene Eq | 0.5M beta- nitro-styrene/ solvent | Reacton temp. T2 °C. | Residence time t2 sec. | Yield (diazo- methane) % |
|---|---|---|---|---|---|---|
| carbitol | 2-propanol | 1.25 | MTBE/heptane (50/50) | 20 | 74 | 41 |

Partial isomerisation of the double bond was detected. The two products that were formed are <5% 3-nitro-4-phenyl-4,5-dihydro-3H-pyrazole and ~36% 3-nitro-4-phenyl-4,5-dihydro-1H-pyrazole.

EXAMPLE 7

In a continuous reactor setup as described in Example 2 the cycloaddition of diazomethane to methyl cinnamate was performed. Diazomethane was prepared by mixing 1.2M KOH/2-propanol (0.5 ml/min) and 0.4M Diazald®/carbitol solution (1.0 ml/min) and reacting them at 60° C. The reaction time was 85 sec. To the homogeneous solution were added continuous streams of NaCl-water (2.0 ml/min) and MTBE/heptane (50/50) (3.0 ml/min) to extract the diazomethane to the organic layer. The organic layer including the diazomethane passes through the membrane where it reacts with the 0.5M methylcinnamate/MTBE-heptane solution at reaction temperature T2 (residence time 49-74 sec). The organic solution was analysed via ¹H-NMR. Results are shown in Table 6.

TABLE 6

| 0.4M Diazald®/ solvent 1.0 ml/min | 1.2M KOH/ solvent 0.5 ml/min | Methyl cinnamate Eq | 0.5M methyl cinnamate/ solvent | Reacton temp. T2 °C. | Residence time t2 sec. | Yield (diazo- methane) % |
|---|---|---|---|---|---|---|
| carbitol | 2-propanol | 1.25 | MTBE/heptane (50/50) | 2 | 74 | 62 |

Partial isomerisation of the double bond is detected. The two isomers that were formed are 10% methyl 4-phenyl-4,5-dihydro-3H-pyrazole-3-carboxylate and 52% methyl 4-phenyl-4,5-dihydro-1H-pyrazole-3-carboxylate.

EXAMPLE 8

A continuous flow (0.50 ml/min) of a solution of 1.0M N-methyl-urea and 1.1M sodium nitrite in water was fed into a flow reactor and continuously mixed with a continuous flow (1.3 ml/min) of 0.5M nitric acid in MTBE/THF/water (96/4/1.5 vol.). After a reaction time of 3 min at 60° C. the reaction mixture entered a flow reactor where it was mixed with a continuous flow (0.6 ml/min) of a solution of 4.0M potassium hydroxide in water. After a reaction time of 30 sec at 0° C. the organic solvent and the formed diazomethane then passed a membrane and were contacted with a flow (1 ml/min) of 1.0M benzoic acid in MTBE/heptane (50/50 vol.). After a reaction time of 2 min at 20° C. the organic phase contained methyl benzoate indicating a yield of 48% based on N-methyl-urea as determined by GC.

The invention claimed is:

1. A process for producing a reaction product of a diazo compound, which process comprises:
   a. continuously supplying to a first reactor a precursor of a diazo compound; a water-miscible solvent; a base and water;
   b. mixing the precursor of a diazo compound; the water-miscible solvent; the base and water to generate a diazo compound;
   c. continuously removing from the first reactor, through a hydrophobic membrane, into a second reactor the formed diazo compound;
   d. continuously removing from the first reactor all reaction products that have not passed into the second reactor;
   e. continuously supplying to the second reactor a substrate in a non-water-miscible solvent;
   f. mixing the above components to generate a reaction product of a diazo compound; and
   g. continuously removing from the second reactor the non-water-miscible solvent and the reaction product of the diazo compound.

2. A process according to claim 1, wherein in step (a) the precursor of a diazo compound; the water-miscible solvent; the base and water are first mixed to form a single feed stream, and then said feed stream is supplied to the first reactor.

3. A process according to claim 1 in which the diazo compound is diazomethane or diazoethane.

4. A process according to claim 1 in which the water miscible solvent is butanol, ethanol, tetrahydrofuran, DMSO or a mixture thereof.

5. A process according to claim 1 in which the base is sodium hydroxide, potassium hydroxide or a mixture thereof.

6. A process according to claim 1, in which the precursor of the diazo compound is N-methyl-N-nitroso-urea, N-ethyl-N-nitroso-urea, N-methyl-N-nitroso-toluene-sulfonamide, N-ethyl-N-nitroso-toluenesulfonamide, N-methyl-N'-nitro-N-nitroso-guanidine, N-ethyl-N'-nitro-N-nitroso-guanidine.

7. A process according to claim 1 in which the membrane is a microporous membrane comprising polypropylene, polytetrafluoroethylene (PTFE) or polyethylene.

8. A process according to claim 1, in which the substrate is an olefin, a ketone, an aldehyde, a carboxylic acid or a carboxylic acid chloride.

9. A process according to claim 1, further comprising,
   h. continuously supplying to a third reactor, an N-alkyl compound, an acid and an aqueous nitrite solution;
   i. mixing the N-alkyl compound, acid and aqueous nitrite solution to generate a precursor of a diazo compound; and
   j. continuously removing from the third reactor the precursor of a diazo compound and continuously supplying it to step (a).

10. A process according to claim 9, comprising in step (h) continuously supplying a non-water-miscible solvent to the third reactor; and, in step (j), optionally separating the aqueous phase from the precursor of the diazo compound and non-water-miscible solvent before supplying the precursor of the diazo compound to step (a).

11. Apparatus suitable for carrying out a process according to claim 1, said apparatus comprising a first reactor separated from a second reactor by a hydrophobic membrane.

12. Apparatus according to claim 11, further comprising a third reactor connected upstream from the first reactor.

13. Apparatus according to claim 12, further comprising a separator comprising a hydrophobic membrane between the third reactor and the first reactor.

14. Apparatus according to claim 11, wherein each of the first, second and, where present, third reactor is a minireactor or a microreactor.

* * * * *